(12) United States Patent
Straub

(10) Patent No.: US 7,453,271 B2
(45) Date of Patent: Nov. 18, 2008

(54) APPARATUS AND METHOD FOR SENSING WATER WITHIN A FUEL-WATER SEPARATOR ASSEMBLY

(75) Inventor: Robert D. Straub, Lowell, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 28 days.

(21) Appl. No.: 11/614,092

(22) Filed: Dec. 21, 2006

(65) Prior Publication Data

US 2008/0150552 A1 Jun. 26, 2008

(51) Int. Cl.
- *G01R 27/08* (2006.01)
- *F02P 17/00* (2006.01)
- *B01D 35/14* (2006.01)
- *F02B 47/02* (2006.01)

(52) U.S. Cl. ............ 324/694; 324/378; 210/89; 123/25 J

(58) Field of Classification Search ............... 324/634, 324/633, 629, 600, 378, 640, 643, 664, 689, 324/694; 210/85, 167.31, 89, 167.08, 110, 210/767, 806, 125, 86, 104, 138, 513; 123/25 J, 123/25 R
See application file for complete search history.

(56) References Cited

U.S. PATENT DOCUMENTS

| | | | | |
|---|---|---|---|---|
| 4,296,723 A | | 10/1981 | Aldrich | |
| 4,328,825 A | * | 5/1982 | Bishai | 137/172 |
| 4,637,351 A | | 1/1987 | Pakula | |
| 5,506,564 A | * | 4/1996 | Hargest | 340/450.2 |
| 5,623,252 A | * | 4/1997 | Cacciola et al. | 340/618 |
| 5,898,375 A | * | 4/1999 | Patterson | 340/612 |
| 5,993,675 A | | 11/1999 | Hagerthy | |
| 6,042,722 A | * | 3/2000 | Lenz | 210/95 |
| 6,170,470 B1 | * | 1/2001 | Clarkson et al. | 123/497 |
| 6,207,045 B1 | * | 3/2001 | Jiang | 210/86 |
| 6,645,372 B2 | * | 11/2003 | Girondi | 210/85 |
| 6,716,349 B2 | | 4/2004 | Baracchi et al. | |
| 6,783,665 B1 | | 8/2004 | Girondi | |
| 6,949,235 B2 | * | 9/2005 | Brown et al. | 423/213.2 |
| 7,143,867 B2 | * | 12/2006 | Chopra | 184/103.2 |
| 2006/0154538 A1 | * | 7/2006 | McCarthy et al. | 440/88 F |

\* cited by examiner

*Primary Examiner*—Vincent Q. Nguyen
*Assistant Examiner*—Hoai-An D Nguyen

(57) ABSTRACT

A method of sensing water within a fuel-water separator assembly disposed within a fuel system of an internal combustion engine is provided. The method includes the steps of: A) monitoring a single selectively activatable sensor within the fuel-water separator assembly to detect the presence of water; B) determining if the sensor is activated for greater than or equal to a first predetermined percentage of time, but less than or equal to a second predetermined percentage of time and providing a first level of warning if true; and C) determining if the sensor is activated for greater than the second predetermined percentage of time and providing a second level of warning if true. An apparatus configured to perform the claimed method is also disclosed.

15 Claims, 2 Drawing Sheets

APPARATUS AND METHOD FOR SENSING WATER WITHIN A FUEL-WATER SEPARATOR ASSEMBLY

TECHNICAL FIELD

The present invention relates to an apparatus and method for sensing water within a fuel-water separator assembly a fuel system operatively connected to an internal combustion engine.

BACKGROUND OF THE INVENTION

Water contamination in hydrocarbon liquid fuels may originate from many sources. Trace amounts of water exist in fuel due to the refining and purification processes performed at the petroleum refineries. Additionally, water may seep into fuel storage tanks or may form as condensation within storage tanks or delivery trucks. Furthermore, when fuel is placed in a fuel tank of a vehicle, water may form through condensation or may be inadvertently introduced into the fuel tank.

Internal combustion engines burning gasoline-type fuels can accommodate relatively large amounts of water before issues such as poor drivability and stalling occur. However, internal combustion engines burning diesel-type fuels are much less tolerant of water mixed with fuel. These engines typically utilize high-pressure pumps and fuel injection devices for introducing pressurized fuel into the internal combustion engine. The pump and injectors are precision devices that are sensitive to water, which has low lubricity and a corrosive effect on metals. From a performance standpoint, water mixed with fuel can cause roughness in engine operation, loss of power, and poor starting ability, particularly during cold start.

The use of fuel-water separator assemblies within fuel systems of internal combustion engines is known in the art. The fuel-water separator assemblies typically include a water reservoir configured to contain water separated from the fuel. A sensor may be provided within the water reservoir to detect the presence of water and to provide a warning to the operator of the vehicle. The control systems used to monitor the sensor typically include a "debounced" type routine operable to ignore the intermittent activation of the sensor due to the sloshing of water with the movement of the vehicle. As such, typical control systems employing a single sensor provide the ability to sense one level, i.e. a critical level, of water within the fuel-water separator.

SUMMARY OF THE INVENTION

A method of sensing water within a fuel-water separator assembly disposed within a fuel system of an internal combustion engine is provided. The method includes the steps of: A) monitoring a single selectively activatable sensor, such as a conductivity-type or float-type sensor, within the fuel-water separator assembly to detect the presence of water; B) determining if the sensor is activated for greater than or equal to a first predetermined percentage of time, but less than or equal to a second predetermined percentage of time and providing a first level of warning if true; and C) determining if the sensor is activated for greater than the second predetermined percentage of time and providing a second level of warning if true.

The first level of warning may be of the form of a visual and/or audible alarm. The second level of warning, which is more critical than that of the first level of warning, may be of the form of at least one of: A) shutting off the internal combustion engine; B) limiting the maximum power of the internal combustion engine; C) limiting the speed of the internal combustion engine; and D) reducing the injection pressure of the fuel system.

An apparatus for sensing water within a fuel-water separator assembly disposed within a fuel system of an internal combustion engine is also provided. The apparatus includes a water reservoir mounted with respect to the fuel-water separator assembly and operable to contain water. A single selectively activatable sensor is mounted with respect to the water reservoir and is operable to detect water within the reservoir. A controller is provided and sufficiently programmed to: A) monitor the sensor to detect the presence of water; B) determine if the sensor is activated for greater than or equal to a first predetermined percentage of time, but less than or equal to a second predetermined percentage of time and command a first level of warning if true; and C) determine if the sensor is activated for greater than the second predetermined percentage of time and command a second level of warning if true.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Figure 1:
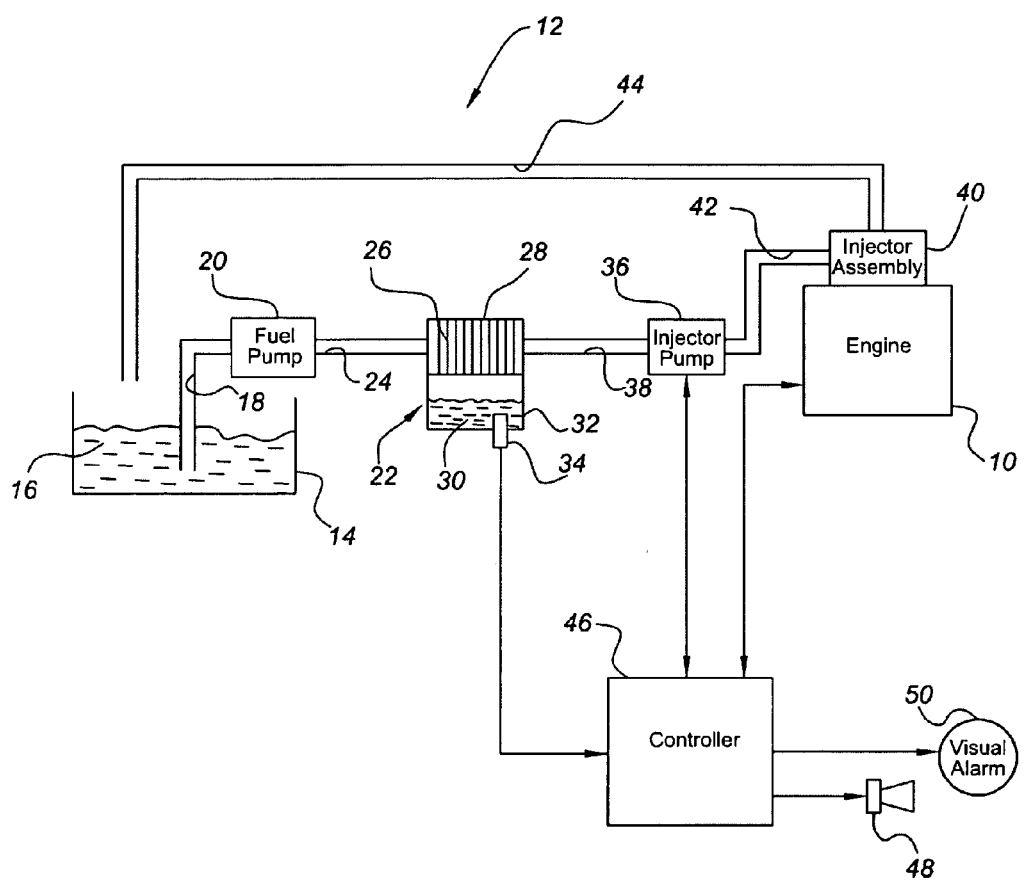
FIG. 1 is a schematic illustration of an internal combustion engine having a fuel system and a controller in accordance with the present invention.

Referring to FIG. 1 there is shown an internal combustion engine 10 having a fuel system, generally indicated at 12, operatively connected thereto. The internal combustion engine 10 of FIG. 1 is a compression-ignited, diesel-fueled engine. However, those skilled in the art will recognized that the claimed invention may be applied to other types of internal combustion engines, such as spark-ignited, gasoline-fueled engines. The fuel system 12 includes a fuel reservoir or tank 14 configured to contain a predetermined amount of fuel 16. A fuel pick up 18 is mounted with respect to a fuel pump 20 and is operable to communicate fuel 16 to the fuel pump 20 where it is subsequently pressurized for delivery to a fuel-water separator assembly 22 through line 24. Although the fuel pump 20 of FIG. 1 is illustrated upstream of the fuel-water separator assembly 22, those skilled in the art will recognize that the fuel pump 20 may be placed downstream of the fuel-water separator assembly 22 while remaining within the scope of that which is claimed.

The fuel-water separator assembly 22 includes a filter element 26 and a water separator 28 configured to remove particulate matter and water 30, respectively, from within the fuel 16. The fuel-water separator assembly 22 has a water reservoir 32 mounted thereto, which is operable to contain the water 30 extracted from the fuel 16 as it passes through the fuel-water separator assembly 22. A sensor 34 is mounted with respect to the water reservoir 32 and is selectively activatable in the presence of water 30. The sensor 34 may be a conductivity-type sensor or a float-type sensor the construction and operation of which are well known to those skilled in the art. Those skilled in the art may recognize additional sensor types that may be employed while remaining within the scope of that which is claimed.

The fuel 16 is communicated to an injector pump 36 from the fuel-water separator assembly 22 through a line 38. The fuel-water separator assembly 22 is preferably placed in close proximity to the injector pump 36 to reduce the likelihood damage caused by contamination of the fuel 16 downstream from the fuel-water separator assembly 22. The injector pump 36 is operable to pressurize the fuel 16 to a high level where it is subsequently communicated to an injector assembly 40 via line 42. The injector assembly 40 includes fuel injectors, not shown, which are operable to selectively and variably inject a predetermined amount of fuel 16 into the internal combustion engine 10 for combustion therein. A return line 44 is provided to recirculate fuel 16 within the fuel system 12.

A controller 46 is provided in communication with the sensor 34 and the internal combustion engine 10. The controller 46 is preferably a pre-programmable microprocessor based unit of a type known to those skilled in the art. The controller 46 is configured to monitor and receive signals from the sensor 34 to determine when the sensor 34 is activated, i.e. when water is present within the water reservoir 32. Additionally, the controller 46 is configured to receive signals from the internal combustion engine 10 thereby monitoring various operating conditions, such as engine speed and engine load, and to provide command signals to affect the operation of the internal combustion engine 10. Furthermore, the controller 46 is operable to provide control signals to the injection pump 36 to affect the injection pressure of the fuel 16 communicated to the injector assembly 40.

Figure 2:
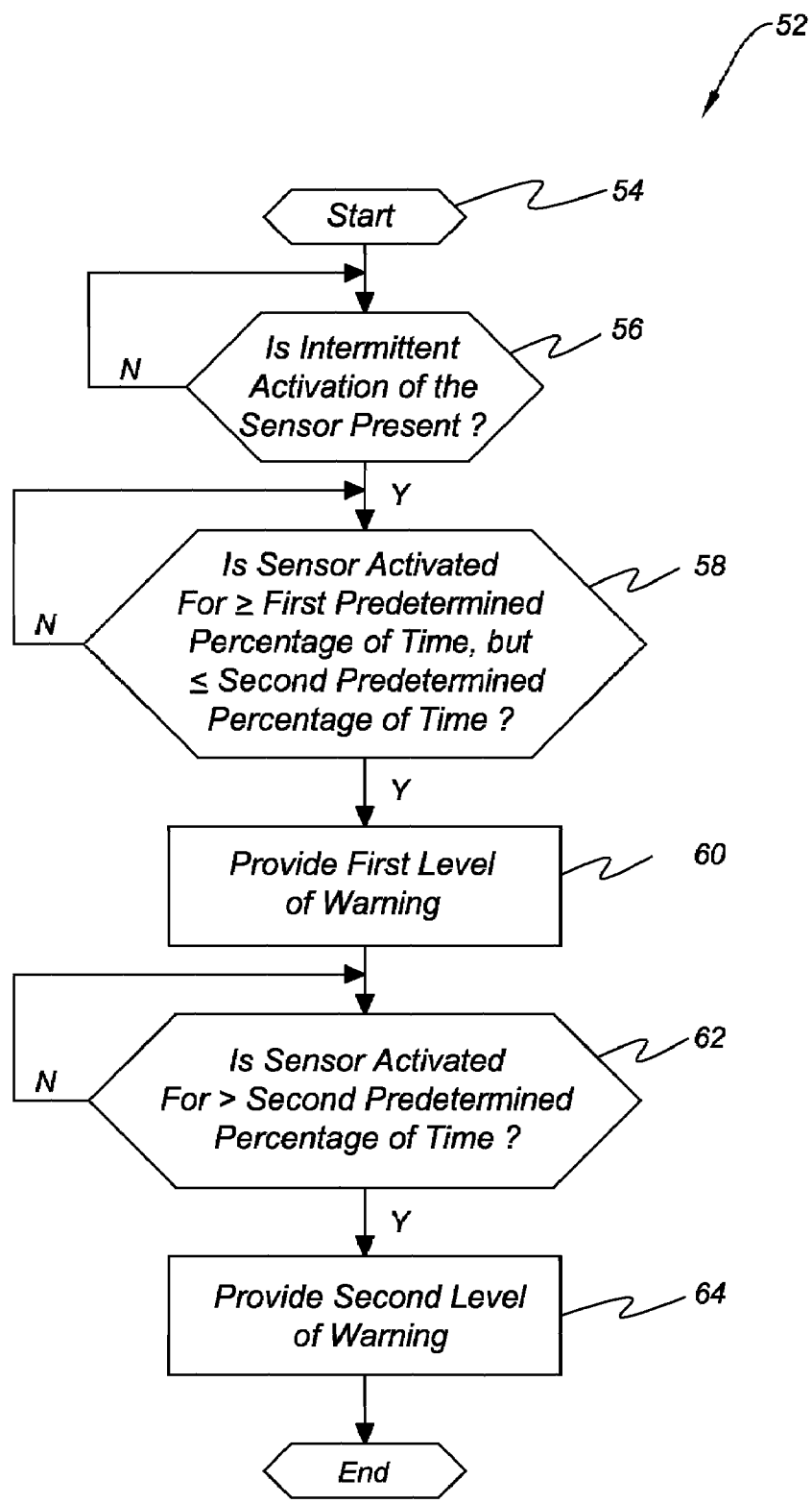
FIG. 2 is a method, in flowchart format, illustrating a method of detecting water within the fuel system of FIG. 1 to be performed by the controller of FIG. 1.

An audible alarm 48, such as a speaker, and a visual alarm 50, such as a light, are controlled by the controller 46 in accordance with a method 52 of FIG. 2 to alert the operator of the vehicle when a predetermined quantity of water 30 is present within the water reservoir 32. Referring to FIG. 2, and with continued reference to FIG. 1, there is shown the method 52 consistent with the present invention. The controller 46 is sufficiently programmed or configured to implement the method 52. The method 52 begins at step 54 and proceeds to step 56 where a determination is made as to whether there is intermittent activation of the sensor 34 as a result of the sloshing of water 30 within the water reservoir 32 due to vehicle movement. If there is no intermittent activation of the sensor 34, the method loops to step 54. Alternately, if there is an intermittent activation of the sensor 34, the method 52 proceeds to step 58 where a determination is made as to whether the sensor 34 is activated for greater than or equal to a first predetermined percentage of time, but less than or equal to a second predetermined percentage of time. The first and second predetermined percentage of time values are predetermined calibration valves derived from experimentation or analysis and will vary with different fuel systems. The percentage of time is determined by the dividing the amount of time the sensor 34 has been activated by the time of operation, i.e. the amount of time the sensor 34 has been activated combined with the amount of time the sensor 34 has been inactive. If the determination at step 58 is false, the method 52 will loop until true. If the determination at step 58 is true, the method 52 proceeds to step 60 where a first level of warning is provided to the operator of the vehicle. The first level of warning indicates that a non-critical level of water 30 has accumulated within the water reservoir 32 and that the water reservoir 32 should be drained. The first level of warning is preferably of the form of a visual and/or audible alert. The first level of warning can be implemented by the controller 46 commanding the operation of the visual alarm 50 and/or the audible alarm 48.

The method 52 then proceeds to step 62 where a determination is made as to whether the sensor 34 is activated for greater than the second predetermined percentage of time. If the sensor 34 is not activated for greater than the second predetermined percentage of time, the method 52 will loop until true. The method 52 then proceeds to step 64 where a second level of warning is provided to the operator indicating that the level of water 30 within the water reservoir 32 has reached a critical level and should be drained. The second level of warning is more critical than that of the first level or warning and as such, the controller 46 may command at least one of: A) shutting off the internal combustion engine 10; B) limiting the maximum power of the internal combustion engine 10; C) limiting the speed of the internal combustion engine 10; and D) reducing the injection pressure of the fuel system 12. The controller 46 will preferably continue to provide the second level of warning until the water 30 has been drained from the water reservoir 32. Additionally, historical information may be stored within the controller 46 for later retrieval, such as the length of time the internal combustion engine 10 was operated with a critical level of water 30 within the water reservoir 32. This historical information may be useful when servicing the internal combustion engine 10 to aid in diagnosing performance issues related to corrosion of the fuel system 12.

The first and second predetermined percentage of time is a calibrated value that must be determined for each of the various types of fuel-water separator assembly and sensor configurations. The method and apparatus of the claimed invention allows the sensing of a non-critical and critical level of water 30 within the water reservoir 32 of the fuel-water separator assembly 22 using a single sensor 34.

While the best modes for carrying out the invention have been described in detail, those familiar with the art to which this invention relates will recognize various alternative designs and embodiments for practicing the invention within the scope of the appended claims.

The invention claimed is:

1. A method of sensing water within a fuel-water separator assembly disposed within a fuel system of an internal combustion engine, the method comprising:
    monitoring a single selectively activatable sensor within the fuel-water separator assembly to detect the presence of water;
    determining if said sensor is activated for greater than or equal to a first predetermined percentage of time, but less than or equal to a second predetermined percentage of time and providing a first level of warning if true; and
    determining if said sensor is activated for greater than said second predetermined percentage of time and providing a second level of warning if true.

2. The method of claim 1, wherein said first level of warning is at least one of an audio alarm and a visual alarm.

3. The method of claim 1, wherein said second level of warning is at least one of shutting off the internal combustion engine, limiting the maximum power of the internal combustion engine, limiting the speed of the internal combustion engine, and reducing the injection pressure of the fuel system.

4. The method of claim 1, wherein said sensor is one of a float type and a conductivity type sensor.

5. The method of claim 1, further comprising continuing to provide said second level of warning until the water within the fuel-water separator is drained.

6. An apparatus for sensing water within a fuel-water separator assembly disposed within a fuel system of an internal combustion engine, the apparatus comprising:

a water reservoir mounted with respect to the fuel-water separator assembly and operable to contain water;

a single selectively activatable sensor mounted with respect to said water reservoir and operable to detect water within said reservoir;

a controller sufficiently programmed to:
   monitor said sensor to detect the presence of water;
   determine if said sensor is activated for greater than or equal to a first predetermined percentage of time, but less than or equal to a second predetermined percentage of time and command a first level of warning if true; and
   determine if said sensor is activated for greater than said second predetermined percentage of time and command a second level of warning if true.

7. The apparatus of claim 6, further comprising:
an audio alarm; and
wherein said controller is configured to activate said audio alarm when said first level of warning is commanded.

8. The apparatus of claim 6, further comprising:
a visual alarm; and
wherein said controller is configured to activate said visual alarm when said first level of warning is commanded.

9. The apparatus of claim 6, wherein said controller is configured to perform at least one of the shutting off of the internal combustion engine, limiting the maximum power of the internal combustion engine, limiting the speed of the internal combustion engine, reducing the injection pressure of the fuel system, and storing historical information when said second level of warning is commanded.

10. The apparatus of claim 6, wherein the internal combustion engine is a compression-ignited engine.

11. The apparatus of claim 6, wherein the internal combustion engine is a spark-ignited engine.

12. The apparatus of claim 6, wherein said sensor is one of a float type and a conductivity type sensor.

13. The apparatus of claim 6, wherein the fuel-water separator assembly includes a filter element.

14. A method of sensing water within a fuel-water separator assembly disposed within a fuel system of an internal combustion engine, the method comprising:
   monitoring a single selectively activatable sensor within the fuel-water separator assembly to detect the presence of water;
   determining if said sensor is activated for greater than or equal to a first predetermined percentage of time, but less than or equal to a second predetermined percentage of time and providing at least one of an audio alarm and a visual alarm if true; and
   determining if said sensor is activated for greater than said second predetermined percentage of time and performing at least one of shutting off the internal combustion engine, limiting the maximum power of the internal combustion engine, limiting the speed of the internal combustion engine, and reducing the injection pressure of the fuel system if true.

15. The method of claim 14, wherein the internal combustion engine is one of a spark-ignited and a compression-ignited internal combustion engine.

* * * * *